United States Patent [19]

Shaw et al.

[11] 4,297,689

[45] Oct. 27, 1981

[54] PERSONNEL-CARRIED DOSIMETER

[75] Inventors: Manuel Shaw, Bel Air; Imbrie Thatcher, Chatsworth, both of Calif.

[73] Assignee: Interscan Corporation, Chatsworth, Calif.

[21] Appl. No.: 110,359

[22] Filed: Jan. 8, 1980

[51] Int. Cl.³ .................... G01N 27/46; G01N 27/54; G08B 23/00
[52] U.S. Cl. .................. 340/632; 204/195 R; 204/195 P
[58] Field of Search .............. 204/195 R, 1 T, 1 K, 204/195 P; 340/632, 633, 634

[56] References Cited

U.S. PATENT DOCUMENTS

| | | | |
|---|---|---|---|
| 3,515,658 | 6/1970 | Amdur | 204/195 P |
| 3,574,048 | 4/1971 | Hynes et al. | 204/195 P |
| 3,776,832 | 12/1973 | Oswin et al. | 204/195 R |
| 4,013,522 | 3/1977 | Nischik et al. | 204/1 T |
| 4,029,563 | 6/1977 | Binder et al. | 204/195 R |
| 4,132,616 | 1/1979 | Tantram et al. | 204/195 P |
| 4,152,233 | 5/1979 | Chand | 204/195 P |
| 4,169,779 | 10/1979 | Tataria et al. | 204/195 P |
| 4,182,666 | 1/1980 | Dickinson et al. | 204/195 P |
| 4,231,249 | 11/1980 | Zuckerman | 340/632 X |

OTHER PUBLICATIONS

Unico Carbon Monoxide Detector & Alarm.

Primary Examiner—G. L. Kaplan
Attorney, Agent, or Firm—Spensley, Horn, Jubas & Lubitz

[57] ABSTRACT

A dosimeter includes an electrochemical sensing cell and circuitry which provides a first alarm when the contaminant concentration exceeds a short-term exposure limit, and a second alarm when the time weighted average concentration level over a relatively longer term exceeds a different threshold limit value. In one sensing cell embodiment, the gas sample flows through a circuitous recess on the interior surface of the cell body, which recess is covered by the sensing electrode. A downstream pump urges the gas sample through the cell. In an alternative embodiment, not utilizing a pump, the gas sample enters the cell by diffusing through a sintered porous plate into contact with the sensing electrode. In each cell, the output current is proportional to the contaminant concentration level.

To obtain a time weighted concentration level alarm signal, the circuitry employs a frequency converter that produces output pulses at a rate proportional to the cell output current level. These pulses are counted. The alarm signal is produced when the count reaches a value $C = LnT$, where n is the frequency converter output in pulses per second for a concentration of 1 ppm, T is a certain extended time duration, and L is the threshold limit value.

17 Claims, 7 Drawing Figures

PERSONNEL-CARRIED DOSIMETER

BACKGROUND OF THE INVENTION

1. Field of the Invention

The present invention relates to a portable gas detection dosimeter carried by an individual to monitor the levels of airborne chemical contaminants to which the individual is exposed, and to provide an alarm when certain short-term or long-term weighted average exposure limits to the contaminant are exceeded.

2. Description of the Prior Art

In many industries workers are exposed to airborne concentrations of chemical substances such as carbon monoxide, sulfur dioxide, hydrogen sulfide, nitrogen oxide or chlorine. If the levels of these contaminants are sufficiently low, the worker may be repeatedly exposed to them day after day without adverse effect. However, if the concentration levels increase sufficiently, exposure to the contaminants may result in physical irritation or impairment of health of the individual.

Such adverse physiological reactions may occur either as a result of short term exposure to relatively high concentrations of the contaminant, or long-term exposure to relatively lower concentrations. Various governmental and other safety standards now are being promulgated to set acceptable limits for such short and long-term exposure to various airborne chemical substances.

One such standard is the "short-term exposure limit" (STEL). This is the maximum concentration to which a worker can be exposed for a period up to fifteen minutes continuously without suffering from irritation, chronic or irreversible tissue change, or narcosis of sufficient degree to increase accident proneness, impair self-rescue, or materially reduce work efficiency. Another standard is the "time-weighted average" (TWA) concentration for a normal eight hour work day or forty-hour work week, to which nearly all workers may be repeatedly exposed, day after day, without adverse effect. Thus the STEL and TWA represent two categories of "threshold limit values" (TLV) which represent maximum allowable exposure limits to the airborne contaminants.

In the past, such contaminant levels have been measured by using an electrochemical monitor placed in the work area. This approach, however, often did not provide an accurate indication of the actual exposure of an individual worker. Since the instrument only measured the contaminant concentration at a single location, it did not indicate the actual levels to which the worker was exposed as he moved from place to place in the course of his work. Thus, e.g., the time weighted average concentration level at the fixed location of the monitor may have been within an acceptable limit, whereas the average contaminant level to which a particular worker was exposed during the work day may have exceeded the acceptable limit, as a result of his periodic incursions into areas of higher concentration.

To alleviate this shortcoming, a principal object of the present invention is to provide a small, portable dosimeter which is carried by the individual worker so as to monitor the actual airborne contaminant levels to which the individual is exposed. Should the short-term or TWA threshold limit values be exceeded, the dosimeter provides an audio and/or visual alarm to warn and notify the individual of the excess exposure condition.

Electrochemical sensing cells for detecting airborne contaminant chemicals are known per se. For example, such a cell is shown in inventors' U.S. Pat. No. 4,017,313. This device consists of a sensing electrode and a counterelectrode, in contact with an electrolyte. When the contaminant gas contacts the sensing electrode, either electrooxidation or electroreduction occurs, depending on the species to be detected. A complementary reaction occurs at the counterelectrode. These reactions cause an electrical current to flow, the magnitude of which is proportional to the contaminant concentration. By appropriate selection of counterelectrode and electrolyte materials, and by using a bias voltage of appropriate potential, the sensing cell may be made selective to a particular gas species.

A shortcoming of prior art electrochemical sensing cells is their relatively large size, which prohibits incorporation into a small, personnel-carried instrument. Thus another object of the present invention is to provide an electrochemical sensing cell having a configuration and small size which permit its incorporation into a portable dosimeter intended for individual use. The electrochemistry of such cell is well known, and indeed is the same as that employed in known cells such as that shown in the inventors° U.S. Pat. No. 4,017,373. However, the cell configurations, including the assemblies utilized to bring air samples into contact with the sensing electrodes, are new and well adapted for use in a dosimeter.

Prior art electrochemical sensing cells of the type described above provide an output current which is proportional to the concentration level present at the cell. That is, the cell itself does not provide an indication of the long-term average concentration level. Rather, this must be obtained by appropriate averaging or integrating circuitry, such as that provided in the dosimeter disclosed herein.

One prior art means for achieving such averaging or integration is by the use of a coulometric device called an "E-cell," which is connected to the output of the electrochemical sensing cell. This silver-nickel device initially is charged like a battery, to a certain charge level. The cell is then exposed to the air, for example, during an eight hour work shift. At the end of this exposure time, the E-cell is discharged at a fixed rate. The amount of time that the E-cell takes to discharge to a reference level is indicative of the time weighted average concentration of the contaminant over the exposure period.

Several disadvantages are inherent in the use of such an E-cell. During the work shift, no indication is provided by the E-cell of the present exposure level. Thus if the worker should be exposed momentarily to a contaminant concentration level which is above the short-term exposure limit, the E-cell will provide no indication of this, and no warning will be given to the worker. Moreover, the time weighted average exposure level can only be obtained at the end of the day when the E-cell is discharged. Thus if the worker is exposed to contaminant levels which exceed the acceptable TWA in less than the full work shift, no indication of this adverse condition will be provided.

By contrast, an object of the present invention is to provide a dosimeter which does not use a coulometric integrating device, but which incorporates appropriate circuitry for use in conjunction with an electrochemical sensing cell to provide an immediate warning to a worker when either the short-term exposure level or the long-term time weighted average acceptable exposure level has been exceeded.

Another object of the present invention is to provide a personnel-carried dosimeter which will maintain a record of the actual contaminant exposure levels to which the worker was exposed during the day. The dosimeter then can be connected to an external readout device, such as a printer, to obtain a record of this contaminant exposure history.

SUMMARY OF THE INVENTION

These and other objectives are achieved by providing a personnel-carried dosimeter incorporating a small electrochemical sensing cell together with appropriate electrical circuitry which produces an alarm in the event that either a preset exposure level has been exceeded on a short-term basis, or that the TWA exposure level has exceeded an acceptable threshold limit value.

To this end, the dosimeter incorporates a sensing cell which, in one embodiment, has a circuitous recess in the interior surface of the cell body. A planar sensing electrode covers this recess. A downstream pump develops a flow of air through the circuitous recess so that airborne contaminant substances will come in contact with a relatively large area of the sensing electrode. Appropriate biasing is used so that the sensing cell then will produce an electrical current proportional to the concentration of the particular substance being monitored.

In an alternative cell embodiment, a porous sintered polymer plate is mounted in a large aperture in the base of the cell. The planar sensing electrode faces this plate. No pump is used. Rather, air diffuses through the sintered polymer plate into direct contact with the sensing electrode. Again, the resulting electrical current is indicative of the concentration level of a particular contaminant species.

The output of the employed sensing cell is provided to two electrical circuits. The first is a high level alarm wherein the cell output signal is compared with another signal of preset level. When the cell output exceeds the preset value, indicating that a particular contaminant exposure level such as the STEL has been exceeded, a comparator provides an output signal which initiates a visual and/or audible alarm. For example, the signal may turn on both a light emitting diode and a buzzer.

The second circuit provides a time weighted average alarm. To this end, a voltage controlled oscillator or like controllable frequency source is used to provide a stream of pulses having a pulse rate directly proportional to the electrochemical sensing cell output. A counter, which is reset at the beginning of the work shift, then counts the pulses from the frequency converter. The contents of the counter is indicative of the time weighted average exposure level. If this count exceeds a certain value within a preset time duration, such as an eight hour work shift, an alarm is sounded to indicate that the acceptable TWA exposure level has been exceeded.

In an alternative embodiment, the dosimeter may include a digital memory for storing, in separate memory locations, the average exposure levels over successive time intervals during the work day. These stored values then may be read out and displayed to obtain a history of the actual exposure levels for each worker.

BRIEF DESCRIPTION OF THE DRAWINGS

A detailed description of the invention will be made with reference to the accompanying drawings wherein like numerals designate corresponding parts in the several figures.

DESCRIPTION OF THE PREFERRED EMBODIMENTS

The following detailed description is of the best contemplated modes of carrying out the invention. This description is not to be taken in a limiting sense, but is made merely for the purpose of illustrating the general principles of the invention since the scope of the invention best is defined by the appended claims.

Operational characteristics attributed to forms of the invention first described also shall be attributed to forms later described, unless such characteristics obviously are inapplicable, or unless specific exception is made.

Figure 1:
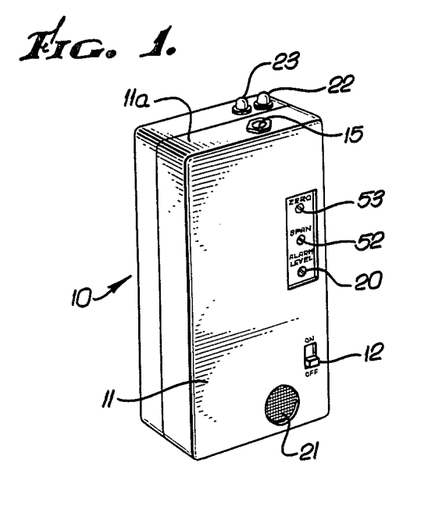
FIG. 1 is a pictorial view of a personnel-carried dosimeter in accordance with the present invention.
Figure 2:
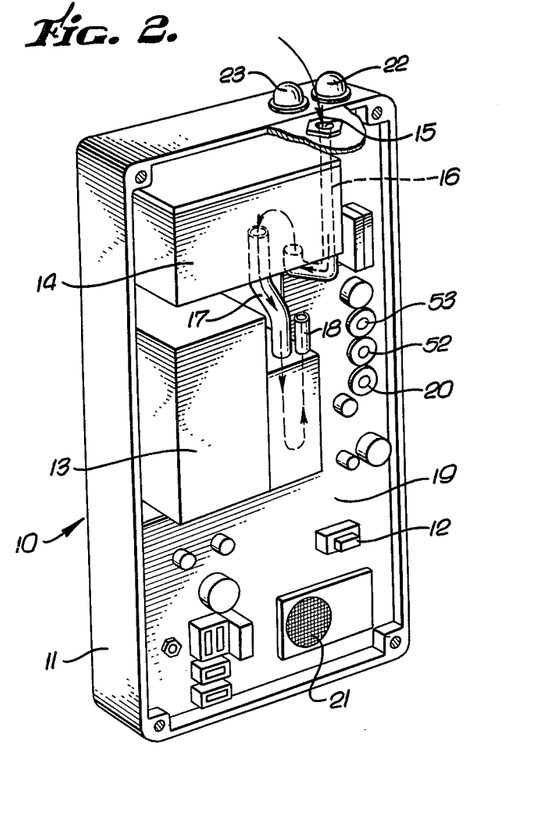
FIG. 2 is a pictorial view of the dosimeter of FIG. 1, but with the cover removed to show the major components.

Referring now to FIGS. 1 and 2, the inventive personnel-carried dosimeter 10 is contained in a case 11 which preferably is small enough to be carried conveniently in the user's pocket. At the beginning of the work shift, the user turns on the dosimeter using the switch 12. He then places the instrument in his pocket, with the upper end 11a of the case 11 exposed to the air.

During the work shift, air is continuously drawn into the dosimeter 10 by a pump 13 situated downstream of an electrochemical sensing cell 14. The sampled air enters through an opening 15 in the case 11, and then follows a flow path including a channel 16, the cell 14, a tube 17, the pump 13, and an outlet tube 18 which leads to an outlet opening (not shown) in the case 11. The cell 14 uses appropriate electrode materials and is biased to be selectively sensitive to a particular contaminant gas species. The concentration of this contaminant in the sampled air entrant through the opening 15 is indicated by the output current from the cell 14.

Appropriate electrical circuitry 19, described below in connection with FIG. 6, utilizes the electrical output from the cell 14 to provide warning signals in the event that short-term or time weighted average long-term exposure levels are exceeded. Thus if the worker is exposed even for a short time to a contaminant level above a value set by a control 20, a buzzer 21 will sound an audible alarm, and a light emitting diode 22 will go on, thereby giving the worker a visible indication that the STEL or other preset high level has been exceeded. Further, the circuitry 19 effectively integrates the output from the sensing cell 14 to obtain an indication of the time weighted average exposure level. Should this TWA value exceed an acceptable threshold limit value, whether or not the short-term exposure level has been exceeded, the buzzer 21 again will sound a warning alarm, and a light emitting diode 23 will go on, to indicate that this TWA threshold limit value has been exceeded.

Figure 7:
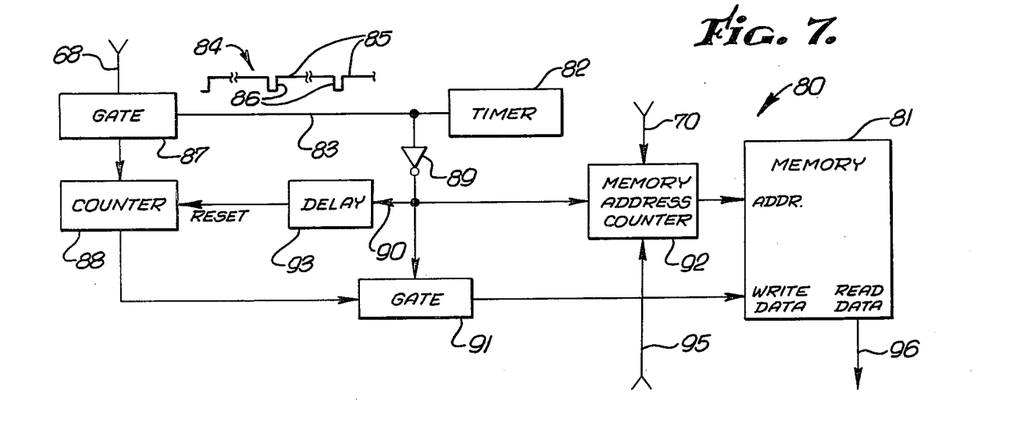
FIG. 7 is an electrical block diagram of optional memory circuitry for use in conjunction with the dosimeter of FIGS. 1 and 2.

In an optional embodiment utilizing the circuitry of FIG. 7, the dosimeter 10 electrically stores a record of the worker's exposure levels during the work shift. At the end of the day, the dosimeter 10 may be connected to an external readout device which prints or otherwise displays the contents of the memory, thereby providing a record of the exposure history during the course of the work day.

Figure 3:
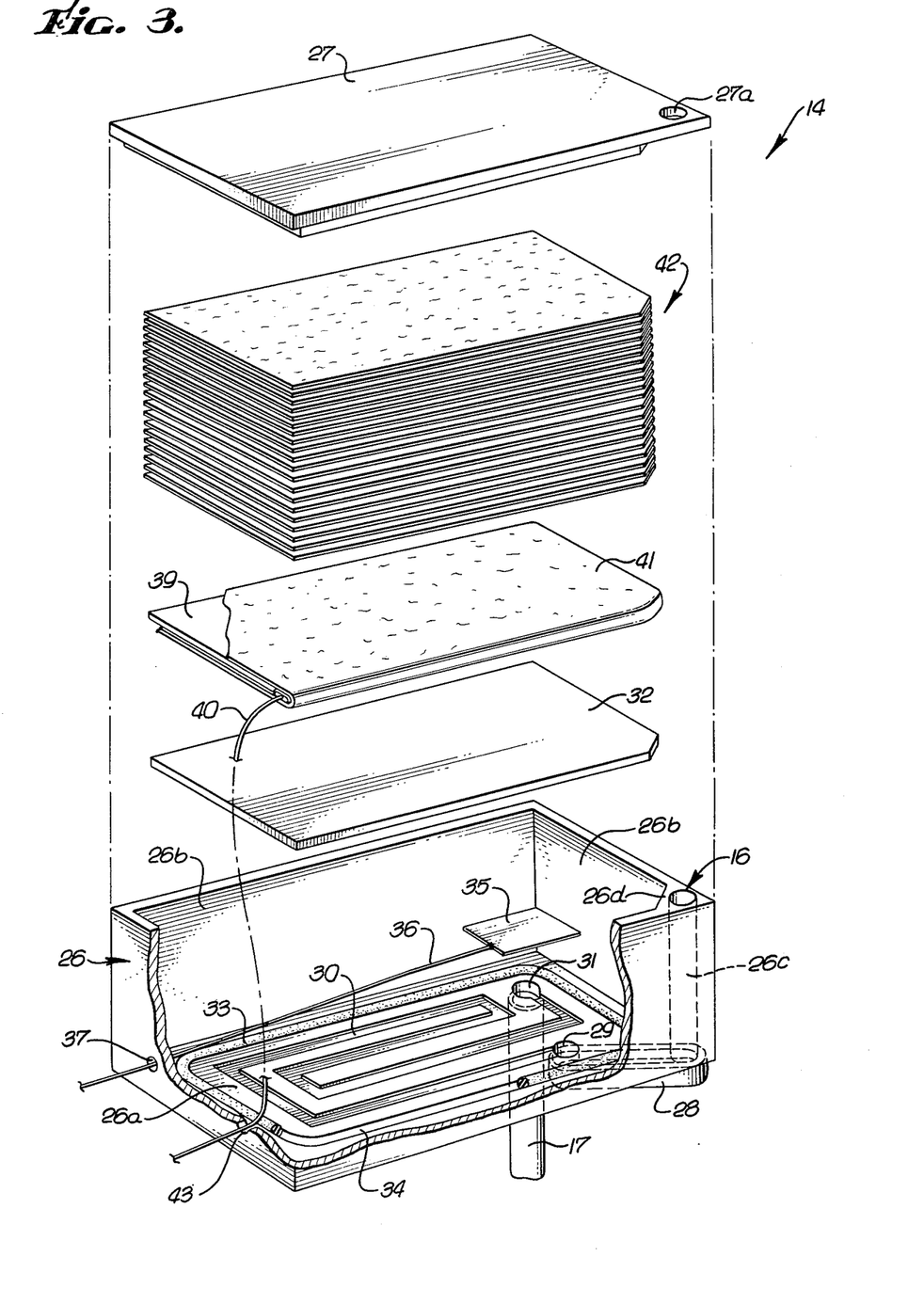
FIG. 3 is an exploded view, partly broken away and in section, of the electrochemical sensing cell used in the dosimeter of FIGS. 1 and 2.

Details of the electrochemical sensing cell 14 are shown in FIG. 3. The cell housing includes a rigid body 26 having a planar base 26a and upright walls 26b. The body 26 is closed by a lid 27. Inlet air is communicated into the cell 14 via the channel 16 which extends through a hole 27a in the lid 27, a bore 26c through a corner portion 26d of the body 26, and a channel member 28 on the outside of the base 26a. The air sample then enters the cell 14 through an inlet port 29 at one end of a circuitous recess 30 on the interior surface of the base 26a. The sample leaves the cell 14 through an outlet port 31 situated at the other end of the recess 30 and communicating to the tube 17.

A planar sensing electrode 32 covers the circuitous recess 30. An O-ring seal 33 seats within a groove 34 in the base 26 surrounding the circuitous recess 30. The underside of the sensing electrode 32 engages the O-ring seal 33, so that the seal forms a barrier which prevents any of the gas sample that is present between the base 26a and the electrode 32 from escaping into the rest of the cell. Indeed, the gas flow primarily is restricted to the circuitous recess 30 itself, and along this recess the sample gas is in direct contact with a substantial area of the sensing electrode 32. Electrical connection to the electrode 32 is provided by means of a platinum or other conductive foil strip 35 which seats between a small portion of the O-ring 33 and the electrode 32. The strip 35 is connected to a wire 36 which leaves the cell 14 through a hole 37 in the wall 26b.

Situated above the sensing electrode 32 is a planar reference electrode 39 having an associated electrical wire 40 which leaves the cell 14 through an opening 43. Advantageously, the reference electrode 39 is wrapped with a glass filter paper 41 which becomes impregnated with the electrolyte (not shown) that fills the interior of the cell 14. The remainder of the cell 14 is filled with layers 42 of electrolyte-impregnated glass filter paper. A sufficient number of layers 42 is used so that when the lid 27 is implaced on the body 26, a compressive force will be exerted by the layers 42 which maintains the sensing electrode 32 in firm sealing contact with the O-ring 33.

In a dosimeter 10 intended for the detection of a contaminant gas such as CO, $SO_2$, $H_2S$, $NO_2$, or $Cl_2$, the sensing electrode 32 may consist of platinum, advantageously in the form of fine particulate platinum powder bonded in a Teflon or other polymeric binder. The reference electrode advantageously is lead, and the electrolyte may be dilute sulfuric acid in water (typically 2.5 molar solution). The wrapping 41 and layers 42 may consist of type 934AH glass fiber filter paper manufactured by Watman, Inc., Clifton, N.J. The cell body 26 and lid 27 may be formed of acrylic or polystyrene, or may be a metal which is not attacked by the electrolyte.

Figure 4:
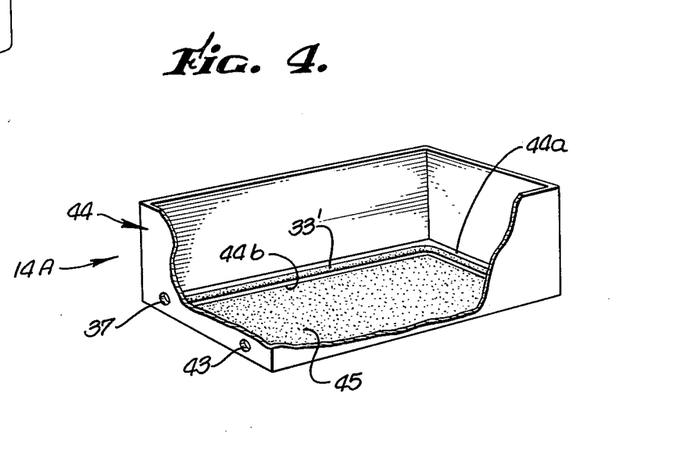
FIG. 4 is a perspective view, partly broken away and in section, of part of an alternative electrochemical sensing cell configuration.
Figure 5:
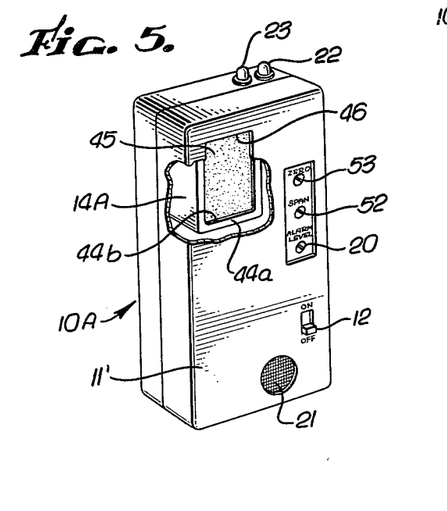
FIG. 5 is a pictorial view, partly broken away and in section, of a dosimeter employing the cell of FIG. 4.

In the alternative embodiment of FIG. 5, the dosimeter 10A uses an electrochemical sensing cell 14A having the configuration shown in FIG. 4. Here the body 44 has a base 44a that has a large opening 44b within the periphery of the O-ring 33'. Completely covering the opening 44b is a plate 45 formed of a porous sintered polymer such as the linear, high density polyethylene material sold under the trademark "Vyon" by Povair, Ltd. of England. The remainder of the cell 14A is the same as that shown in FIG. 3. That is, the cell 14A utilizes a like sensing electrode 32, foil strip 35, conductor 36, reference electrode 39, conductor 40, wrapping 41, filter papers 42, electrolyte and lid 27 in the same arrangement as shown in FIG. 3. Alternatively the porous plate 45 and seal 33' may be placed in the lid (not shown) of the cell, and the remaining contents of the cell 14A may be arranged in reverse order from that shown in FIG. 3.

In contrast with the cell 14 of FIG. 3, however, there is no need to pump the gas sample through the sensing cell 14A. Thus the dosimeter 14A does not employ a pump 13. Rather, the cell 14A is mounted within the case 11' with the outside of the base 44a and plate 45 exposed to the ambient air through a window 46 in the case 11'. Air diffuses through the plate 45 into direct contact with the sensing electrode 32. The O-ring 33' prevents gas leakage into the remainder of the cell 14A. Again, the electrical current developed between the conductors 36 and 40 is proportional to the concentration of the contaminant species in the air sample.

Figure 6:
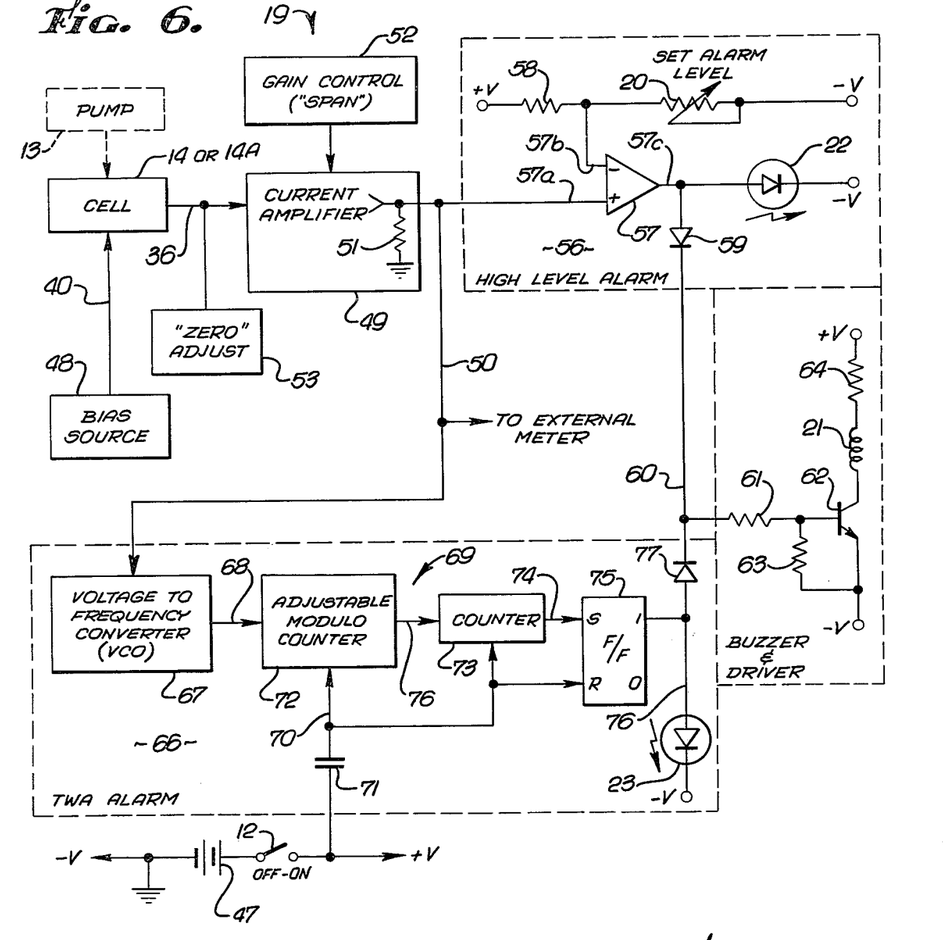
FIG. 6 is an electrical schematic diagram of the inventive dosimeter showing both the high level alarm and TWA alarm circuits.

One embodiment of the circuitry 19 is shown in FIG. 6. When the switch 12 is closed, voltage from a battery 47 is supplied to the circuitry 19. A bias source 48 is energized which provides to the reference electrode 39, via the line 40, a voltage appropriate to ensure that only a particular species of contaminant gas is selected. Accordingly, the concentration of this species at the cell 14 or 14A will be indicated by the magnitude of the current supplied from the sensing electrode 32 on the line 36.

This current is amplified by an amplifier 49 the output 50 of which appears across a resistor 51 of fixed value. Accordingly, the voltage drop across the resistor 51 will be directly proportional to the current from the cell 14 or 14A. Thus the level of voltage on the output line 50 will be directly proportional to the concentration of the contaminant species being measured.

The gain of the amplifier 49 may be adjusted using a control 52. This control 52 is sometimes called a "span" adjustment, since it is used to set the output of the amplifier 49 to a specific voltage level when a known concentration of the contaminant species is present at the cell 14 or 14A. A "zero" adjustment circuit 53 also is associated with the input to the amplifier 49. This circuit 53 enables the amplifier 49 output to be set at zero when no contaminant gas is present at the cell 14 or 14A. In a typical embodiment, the amplifier 49 may comprise a conventional integrated circuit operational amplifier in which the cell output line 36 is connected to the input of the non-inverting (+) input and the zero adjust circuit 53 is connected to the inverting (−) input. Then, with no contaminant gas present at the cell 14 or 14A, the zero adjust circuit 53 is set to provide sufficient current to the operational amplifier so that the voltage on the output line 50 will be zero.

Short term exposure to contaminant levels above an acceptable threshold limit value is detected by a high level alarm circuit 56. An operational amplifier 57 receives as one input 57a the voltage on the line 50 which is indicative of the contaminant gas concentration present at the cell 14 or 14A. The other input 57b is a reference voltage provided from a voltage divider consisting of a resistor 58 and the alarm level setting potentiometer 20. This control 20 is set so that the amplifier 57 will provide a low output on a line 57c until the contaminant gas level exceeds a certain value. When that level is exceeded, the input voltage on the line 50 will be greater than that on the reference line 57b, and the amplifier output 57c will go high. As a result the light emitting diode 22 will go on, and the buzzer 21 will sound an alarm.

To actuate the buzzer 21, the high signal on the line 57c is supplied via a diode 59, a line 60 and a resistor 61 to the base of a transistor 62. When this occurs, the bias voltage developed across a resistor 63 turns on the transistor 62, thereby connecting the buzzer 21 to the battery 47 via a resistor 64 and the conducting transistor 62. A timer (not shown) may be used to limit the duration that the buzzer is on, and thereby minimize battery drain.

A TWA alarm circuit 66 actuates the buzzer 21 and turns on the light emitting diode 23 when the time weighted average concentration of the contaminant species exceeds an acceptable threshold limit value. To accomplish this, a voltage-to-frequency converter 67 provides on a line 68 a train of pulses having a pulse rate proportional to the voltage on the line 50, and hence proportional to the contaminant concentration sensed by the cell 14 or 14A. The converter 67 may be implemented by a conventional voltage controlled oscillator. The total number of pulses produced on the line 68 over a certain time interval is directly indicative of the time weighted average contaminant concentration over that interval.

In the circuit 66, the pulses on the line 68 are counted by a counter 69 which is set to zero when the dosimeter 10 or 10A is turned on. For this purpose, a reset pulse is obtained on a line 70 via a capacitor 71 when the switch 12 first is turned on. The counter 69 advantageously, but not necessarily, consists of an adjustable modulo counter 72 connected in cascade with a fixed modulo counter 73. Appropriate selection of the modulo of the counter 71 has the effect of setting the time weighted average level at which an alarm will be sounded. This alarm will occur when the cumulative number of pulses supplied on the line 68 equals that total count value of the counter 69. At that time, the counter 69 will provide an output pulse on a line 74 which will set to "1" a flip-flop which had been reset to "0" when the switch 12 first was turned on. Setting of the flip-flop 75 will produce a high output on a line 76 which will turn on the light emitting diode 23, and will be supplied by a diode 77 to the line 60 so as to turn on the buzzer 21.

The following example illustrates the operation of the TWA alarm circuit 66. For a particular contaminant species, the signal on the line 50 will increase by one millivolt (mv) for each one part per million (ppm) increase in contaminant concentration, beginning at zero volts when no contaminant is present. Thus, e.g., a contaminant level of 35 ppm will result in a signal of 35 mv on the line 50.

Further, the converter 67 may produce in a unit interval of time (e.g., one second) a number of pulses equal to three times the voltage in millivolts present on the line 50. For example, if the contaminant gas concentration is one ppm, resulting in a one mv signal on the line 50, three pulses per second will be produced on the line 68. For a contaminant level of 35 ppm, with a corresponding voltage of 35 mv on the line, the converter 67 will produce $(35 \times 3) = 105$ pulses per second on the line 68.

The modulo of the counter 72 will be set in accordance with the acceptable TWA threshold limit value for the contaminant species. If this long-term threshold limit value is say 50 ppm, this means that the concentration level can be as high as 50 parts per million for the entire work shift. In other words, a TWA alarm signal should only occur if the averaged concentration level were to exceed the equivalent of a constant 50 millivolts on the line 50 (corresponding to a constant 50 ppm concentration at the cell 14 or 14A) over the entire work shift. For an eight hour workday, this would be the equivalent of having the converter 67 provide as an output $(3 \times 50) = 150$ pulses per second for eight hours or a total of (150 pulses/sec $\times$ 8 hours $\times$ 3600 sec/hr) = $4.32 \times 10^6$ pulses.

Accordingly, the counter 69 is adjusted so that a single output pulse will occur on the line 74 after approximately $4.32 \times 10^6$ pulses have occurred on the line 68. This arrangement can be implemented by adjusting the counter 72 to have a modulo of 132 (so that it will produce a single output pulse on the line 76 to the counter 73 for each 132 pulses on the line 68), and configuring the counter 73 to divide by $2^{15} = 32,768$. As a result, an output will occur on the line 74 when approximately $4.32 \times 10^6$ pulses have occurred on the line 68. That is, the flip-flop 75 will be set, and the TWA alarm will be sounded when the contaminant concentration level at the cell 14 or 14A, on a time weighted average basis, exceeds the TLV of 50 ppm.

Note in the foregoing example that if this maximum TVL acceptable contaminant level of 50 ppm were continuously present throughout the eight hour workday, no pulse would occur on the line 74 during that eight hour interval. However, at the end of that eight hour period, the contents of the counter 69 will just reach the approximate value of $4.32 \times 10^6$ at which the alarm will be set off. If at any time during the day the concentration should rise even slightly above the 50 ppm TLV, and then return to that level, the acceptable TWA will in fact be exceeded within the eight hour period. Under these conditions, however, the contents of the counter 69 will reach the value at which a signal is produced on the line 74 within the eight hour period. When this occurs, the flip-flop 75 will be set, the TWA alarm will be sounded, and the light emitting diode 23 will go on exactly as requird. Of course, the TWA alarm also will be sounded in the instance where the contaminant level for part of the workday remains well under 50 ppm, but for the remaining part of the day is so far in excess of 50 ppm that the TWA threshold limit value will be exceeded. In this instance the counter 69 will reach its maximum count, thereby triggering the TWA alarm, within the eight hour period.

Note that the high level alarm 56 operates independently of the TWA alarm 66. This is important in a situation where the short-term exposure level is exceeded even though the time weighted average exposure level is within acceptable bounds. In this instance, the circuit 56 will produce an alarm signal indicating that the STEL has been exceeded, even though the TWA is within acceptable limits so that the circuit 66 does not produce an alarm.

By using the optional circuity 80 of FIG. 7, the dosimeter 10 or 10A can store a record of the contaminant exposure levels during the entire shift. To this end, a digital memory 81 stores in separate locations numbers indicative of the average contaminant gas concentration levels for consecutive like time intervals during the work shift.

The duration of each time interval for which the average contaminant level is stored is established by a timer 82. For example, the timer 82 may provide on a line 83 a rectangular wave signal illustrated by the waveform 84, and having an on-time 85 of 112 seconds followed by an off-time 86 of 0.5 seconds. With this arrangement, there will be 256 consecutive on-times 85 (each of 112 second duration) during an eight hour period. By measuring the average contaminant level during each such 112 second interval, a total of 256 measurements will be taken during the eight hour workday, and these can be individually stored by a memory 81 having a corresponding 256 storage locations.

To accomplish each measurement, the high signal on the line 83 opens a gate 87 so as to supply the pulses from the frequency converter 67 via the line 68 to a counter 88 that is cleared after each measurement. Since the gate 87 will be open for the time duration of each high signal 85 (for example, 112 seconds), the contents of the counter 88 at the end of such interval will be direct measure of the average contaminant concentration level during the corresponding time interval.

At the end of each measurement interval, when the signal on the line 83 goes low, an inverter 89 will provide a corresponding high signal on the line 90. This will enable a gate 91 to enter the contents of the counter 88 (indicative of the present concentration level) into a storage location of the memory 81 specified by a memory address counter 92. Advantageously, the counter 92 is reset to zero by the reset pulse on the line 70 when the dosimeter 10 or 10A is turned on. The counter 92 then is incremented by the pulse on the line 90 at the end of each measurement interval 85. Accordingly, the contents of the counter 92 will correspond to the ordinal number of the particular measurement (i.e., a first, second . . . 256th) during the workday. As a result, the average contaminant concentration levels during each consecutive measurement interval will be stored in corresponding, consecutively addressed storage locations in the memory 81. After each entry is made to the memory 81, the counter 88 is reset by the pulse on the line 90, slightly delayed in a delay unit 93. Thus the counter 88 is cleared at the beginning of each measurement interval. At the end of the work shift, the memory 81 contains a complete exposure history for the work shift.

At the end of the workday, the stored contaminant exposure history may be accessed from the memory 81 and displayed or printed to produce a written record. To accomplish this, an external readout device (not shown) may supply signals on a line 95 initially to reset and then to increment the memory address counter 92. As each consecutive memory 81 storage location is accessed, the contaminant level stored therein is read out to the external printer via a line 96. The resultant printed out data will represent the average contaminant exposure level for the worker during each of the consecutive measurement time intervals.

The dosimeter 10 or 10A also may be used with an external meter (not shown) to provide a continuous display of the actual contaminant concentration level. To this end, an appropriate connector (not shown) may be provided on the case 11 for electrical connection between the line 50 and an external voltmeter. The level indicated by the voltmeter will be directly proportional to the concentration of the contaminant gas at the electrochemical sensing cell 14 or 14A.

We claim:

1. An electrochemical sensing cell for use in a dosimeter, comprising:
    a housing including a body having a planar base and upright sides extending therefrom to define an interior region and a lid emplaceable atop said sides to enclose said interior region,
    a zigzag recess in said base opening into said interior region, together with a pair of openings through said body at the respective ends of said recess, said openings serving respectively as inlet and outlet ports for the flow of gas through said cell,
    a generally planar sensing element disposed in said body interior region atop said base, gas entrant to the cell through said inlet port flowing throgh said zigzag recess in contact with said sensing electrode along substantially the entire length of said recess, said gas then exiting through said outlet port,
    a reference electrode and an electrolyte also disposed within said interior region, the electrical current developed across said sensing and reference electrodes in the presence of a certain contaminant in said gas being indicative of the concentration of that contaminant in the gas,
    an annular seal between said base and said sensing electrode and surrounding said zigzag recess, said seal limiting the flow of gas between said base and said sensing electrode to within a perimeter defined by said seal, and
    a flow channel extending from said inlet port along the exterior of said base and thence through at least one of said walls and through said lid, gas thereby being supplyable to said recess via said channel from a location atop said lig.

2. A dosimeter contained in a package and comprising:
    an electrochemical sensing cell according to claim 1, said sensing cell being mounted within said package with the lid of said cell adjacent an exterior wall of said package, there being an opening through said package wall communicating to said channel for the inlet flow of gas from outside said package into said cell,
    a pump mounted within said package and connected to said outlet port by a tube, operation of said pump causing a gas sample to be measured by said dosimeter to enter said sensing cell through said inlet port, to flow through said zigzag recess and thence out through said outlet port and pump, and
    circuit means, contained within said package and responsive to said current from said cell, for providing respective alarm signals when the short-term or time weighted average long term contaminant concentration exceeds respective threshold limit values.

3. An electrochemical sensing cell for use in a dosimeter, comprising:
    a housing including a body having a planar base and upright sides extending therefrom to define an interior region and a lid emplaceable atop said sides to enclose said interior region,
    an opening in said base, and a porous plate of sintered polymer covering said opening, said base having only a relatively narrow peripheral portion, said opening comprising the remainder of said base, a generally planar sensing element disposed in said body interior region atop said base, gas being entrant into said cell by diffusion through substantially the entire area of said plate into contact with said sensing electrode, a reference electrode and an electrolyte also disposed within said interior region, the electrical current developed across said sensing and reference electrodes in the presence of a certain contaminant in said gas being indicative of the concentration of that contaminant in the gas, an annular seal between said peripheral portion and said sensing electrode and surrounding said porous plate, said seal preventing the flow of diffused gas from the region between said porous plate and said sensing electrode to the remainder of the cell interior region, a planar, electrically conductive contact situated between a portion of said seal and said sensing electrode, a first electrical wire extending through said body and electrically bonded to said planar contact, said sensing electrode pressing against said planar contact in said cell so that electrical current flow from said sensing electrode is via said planar contact and the associated electrical wire, and a second electrical wire extending through said body into connection with said reference electrode.

4. An electrochemical sensing cell according to claim 3 wherein said sensing electrode comprises particulate platinum bonded together in a plastic matrix, wherein said planar contact is platinum, wherein said reference electrode is lead, and wherein said electrolyte is dilute sulfuric acid.

5. An electrochemical sensing cell according to claim 3 wherein said reference electrode is planar and is disposed atop and separated from said sensing electrode by a fibrous layer, together with additional fibrous layers disposed within said body interior region between said reference electrode and said lid, there being sufficient such layers so as to provide pressure against said reference electrode and said sensing electrode when said lid is emplaced, said pressure maintaining said sensing electrode in electrical contact with said planar contact, said fibrous layers all being impregnated with said electrolyte.

6. A dosimeter comprising:

an electrochemical sensing cell and means for enabling the entry of a gas sample into said sensing cell, the current from said cell indicating the concentration of a certain contaminant species in said gas sample, a "high level" alarm circuit means, connected to said cell, for providing a first alarm signal when the current from said cell indicates that the present concentration of said certain contaminant species exceeds a first threshold limit value, and a "time weighted average" alarm circuit means, also connected to said cell and operative over a certain extended time duration, for providing a second alarm signal when the current from said cell, effectively integrated over a time interval less than or equal to said certain duration, indicates that the time weighted average concentration level of said contaminant species has exceeded a second threshold limit value during that interval, said "time weighted average" alarm circuit means including:

a frequency converter, cooperatively connected to said cell, for providing an output pulse signal having a frequency proportional to the current from said cell, and a counter connected to count the pulses from said frequency converter, said second alarm signal being produced when the count of said counter reaches a preset value within said certain extended time duration.

7. A dosimeter according to claim 6 wherein:

said frequency converter provides n pulses per second for a concentration of one part per million of said certain contaminant species, wherein said certain extended time duration is T seconds, wherein said second threshold limit value is L parts per million, and wherein said "time weighted average" alarm circuit produces said second alarm signal when said counter reaches a count $C = LnT$.

8. A dosimeter according to claim 6 wherein said "high level" alarm comprises:

a comparator, one input of said comparator being a signal proportional to the current from said cell, and alarm level setting means for providing a settable reference signal to the other input of said comparator, said reference signal being set at a level so that said current proportional signal will exceed said set reference signal level, and thereby cause said comparator to provide a certain output, when the concentration of said contaminant species exceeds said first threshold limit level, said first alarm signal being produced in response to occurrence of said comparator certain output.

9. A dosimeter according to claim 6 and contained in a case, said dosimeter further having an audible alarm that is actuated in response to the occurrence of either of said first and second alarm signals, and having separate visual indicators independently respectively actuated by said first and second alarm signals.

10. A dosimeter comprising:

an electrochemical sensing cell which produces an output signal that is proportional in level to the concentration of a contaminant species in a gas sample, and an alarm circuit for producing an alarm signal when the time weighted average concentration level of said contaminant species over a certain extended time duration exceeds a threshold limit value, said alarm circuit including:

a frequency converter, cooperatively connected to said cell, for providing output pulses having a frequency proportional to the signal level from said sensing cell, and a counter connected to count the pulses from said frequency converter, said alarm signal being produced when said counter reaches a preestablished count value within a time interval less than or equal to said certain extended time duration.

11. A circuit according to claim 10 wherein:

said frequency converter provides n pulses per second for a concentration of one part per million of said contaminant species, wherein said certain extended time duration is T seconds, wherein said threshold limit value is L parts per million, and wherein said alarm circuit produces said alarm signal when said counter reaches a preestablished count value $C=LnT$.

12. A circuit according to claim 10 further comprising:
means for modifying said counter so as to set said preestablished count value.

13. A circuit according to claim 12 wherein said counter comprises a first counter of adjustable modulo in cascade with a second counter of fixed modulo, the modulo of said first counter being set by said means for modifying.

14. A dosimeter comprising:
an electrochemical sensing cell which produces an output signal having a level that is indicative of the concentration of a contaminant species in a gas sample,
a frequency converter, cooperatively connected to said cell, for providing output pulses having a frequency proportional to the signal level from said sensing cell,
counter means, connected when enabled to count output pulses from said frequency converter,
timing means for enabling counting by said counter means in consecutive time intervals, each of fixed length, during an extended time duration,
memory means, cooperating with said counter means and said timing means, for storing in separate storage locations the count reached by said counter means in each of said respective consecutive time intervals, the contents of said memory storage locations thereby representing a history of the time weighted average concentration levels of said contaminant species over said consecutive time intervals,
said electrochemical sensing cell including:
  a housing including a body having a planar base and upright sides extending therefrom to define an interior region and a lid emplaceable atop said sides to enclose said interior region,
  an opening in said base, and a porous plate of sintered polymer covering said opening,
  a generally planar sensing element disposed in said body interior region atop said base, gas being entrant into said cell by diffusion through substantially the entire area of said plate into contact with said sensing electrode, and
  a reference electrode and an electrolyte also disposed within said interior region, said output signal being an electrical current developed across said sensing and reference electrodes in the presence of said contaminant species.

15. A personnel-carried dosimeter, comprising:
an electrochemical sensing cell and means for enabling the entry of a gas sample into said sensing cell, the current from said cell indicating the concentration of a certain contaminant species in said sample,
a frequency converter, cooperatively connected to said cell, for providing output pulses having a frequency proportional to the current from said sensing cell,
counter means for counting, when enabled, the output pulses from said frequency converter,
timing means for enabling counting by said counting means during consecutive time intervals each of a fixed duration, and
memory means, cooperating with said counter means and said timing means, for storing in separate storage locations the count reached by said counter means in each of said respective consecutive time intervals, the contents of said memory storage locations thereby representing a history of the time weighted average concentration levels of said contaminant species over said consecutive time intervals.

16. A dosimeter according to claim 15, together with:
readout means, external to said dosimeter but connected thereto, for reading out the contents of said separate storage locations, thereby to recover said history.

17. A dosimeter comprising:
an electrochemical sensing cell which produces an output signal having a level that is indicative of the concentration of a contaminant species in a gas sample,
a frequency converter, cooperatively connected to said cell, for providing output pulses having a frequency proportional to the signal level from said sensing cell,
counter means, connected when enabled to count output pulses from said frequency converter,
timing means for enabling counting by said counter means in consecutive time intervals, each of fixed length, during an extended time duration,
memory means, cooperating with said counter means and said timing means, for storing in separate storage locations the count reached by said counter means in each of said respective consecutive time intervals, the contents of said memory storage locations thereby representing a history of the time weighted average concentration levels of said contaminant species over said consecutive time intervals,
said electrochemical sensing cell including:
  a housing including a body having a planar base and upright sides extending therefrom to define an interior region and a lid emplaceable atop said sides to enclose said interior region,
  a zigzag recess in said base opening into said interior region, together with a pair of openings through said body at the respective ends of said recess, said openings serving respectively as inlet and outlet ports for the flow of gas through said cell,
  a generally planar sensing element disposed in said body interior region atop said base, gas entrant to the cell through said inlet port flowing through said circuitous recess in contact with said sensing electrode along substantially the entire length of said recess, said gas then exiting through said outlet port, and
  a reference electrode and an electrolyte also disposed within said interior region, said output signal being an electrical current developed across said sensing and reference electrodes in the presence of said certain contaminant species.

* * * * *